(12) United States Patent
Thomas et al.

(10) Patent No.: US 7,267,644 B2
(45) Date of Patent: Sep. 11, 2007

(54) PORTABLE ELECTROTHERAPY DEVICE

(75) Inventors: Alex W. Thomas, London (CA); Lynn D. Keenliside, Lucan (CA)

(73) Assignee: Fralex Therapeutics, Inc., London, Ontario (CA)

( * ) Notice: Subject to any disclaimer, the term of this patent is extended or adjusted under 35 U.S.C. 154(b) by 0 days.

(21) Appl. No.: 10/536,411

(22) PCT Filed: Nov. 25, 2003

(86) PCT No.: PCT/CA03/01819

§ 371 (c)(1),
(2), (4) Date: Sep. 20, 2005

(87) PCT Pub. No.: WO2004/047920

PCT Pub. Date: Jun. 10, 2004

(65) Prior Publication Data

US 2006/0106274 A1    May 18, 2006

Related U.S. Application Data

(60) Provisional application No. 60/429,240, filed on Nov. 25, 2002.

(51) Int. Cl.
*A61N 1/00* (2006.01)

(52) U.S. Cl. .................................................. 600/13
(58) Field of Classification Search ............... 600/9–15
See application file for complete search history.

(56) References Cited

U.S. PATENT DOCUMENTS 5,634,939 A    6/1997    Kuster et al.
6,312,376 B1    11/2001    Koren et al.

FOREIGN PATENT DOCUMENTS

EP              1 138 348       10/2001
WO          WO 00 07664 A       2/2000
WO          WO 00 76582        12/2000

*Primary Examiner*—John P. Lacyk
(74) *Attorney, Agent, or Firm*—John S. Child, Jr.

(57) ABSTRACT

The invention discloses an electrotherapy device for generating specifically designed low frequency pulsed magnetic fields (Cnp waveforms). The device comprises a memory storing at least one digital Cnp waveform and a digital to analog converter converting the at least one digital Cnp waveform into an analog Cnp waveform for application to a subject. A processor communicates with the memory and is responsive to operator input and conditioning the memory to output the at least one digital Cnp waveform directly to the digital to analog converter thereby to bypass the processor. The electrotherapy device is useful for electrotherapy of a subject to modify a variety of clinical physiological, neurological and behavioural conditions.

25 Claims, 9 Drawing Sheets

PORTABLE ELECTROTHERAPY DEVICE

CROSS REFERENCE TO RELATED APPLICATIONS

This application is a National Phase entry of PCT/CA2003/001819 filed on Nov. 25, 2003 entitled PORTABLE ELECTROTHERAPY DEVICE by the same inventors which claims the benefit of US Provisional Patent Application, Ser. No.: 60/429,240 which was filed on Nov. 25, 2002 by the same inventors.

FIELD OF THE INVENTION

The present invention relates generally to electrotherapy and in particular to a portable electrotherapy device for generating specifically designed low frequency pulsed magnetic fields that are used to modify a variety of clinical physiological, neurological and behavioural conditions in vertebrates and invertebrates.

BACKGROUND OF THE INVENTION

Diverse studies have shown that the behavioural, cellular and physiological functions of animals can be affected by magnetic stimuli. Weak magnetic fields exert a variety of biological effects ranging from alterations in cellular ion flux to modifications of animal orientation and learning, and therapeutic actions in humans.

There are several theories addressing the mechanism of the effect of low frequency magnetic field exposure on tissues. For example, low frequency magnetic field exposures have been proposed to exert their effect(s) through the induction of electric currents. Weak magnetic fields have also been proposed to be detected by particles of magnetite in tissue and by virtue of this detection, have a physiological effect; however, this magnetite based mechanism is not widely believed (Prato, F. S.; Kavaliers, M.; Carson, J. L. L. (1996) Behavioral evidence that magnetic field effects in the land snail, Cepaea nemoralis, might not depend on magnetite or induced electric currents. Bioelectromagnetics. 17:123-130.).

Extremely low frequency (ELF) magnetic fields are a physical agent which have little attenuation in tissue and therefore, can be used to alter endogenous processes provided they can be detected and their detection coupled to a physiological process. It has now been shown that magnetic fields may be designed as time varying signals such that they can be used to alter specific targeted physiological processes and in this manner can be used to treat/modify various neurological and physiological conditions and behaviours. U.S. Pat. No. 6,234,953 to Thomas et al., the contents of which are incorporated herein by reference, discloses such a method of using low frequency magnetic pulses to treat physiological, neurological and behavioural disorders.

Devices for generating electromagnetic waveforms to stimulate a subject are also known. For example, U.S. Pat. No. 6,312,376 to Koren et al. discloses an apparatus for generating electromagnetic waveforms that includes a signal generator and a selector. The selector applies mathematically-derived waveforms generated by the processor of the signal generator onto selected channels in response to channel select input. The generated waveforms are applied to electromagnetic devices thereby to expose a subject wearing the electromagnetic devices to the generated electromagnetic waveforms. Although this apparatus is satisfactory, improvements are desired.

PCT Application Publication No. WO 96/11723 to Edwards et al. discloses an electromagnetic therapy device that stores waveform parameters such as pulse width, duration, duty cycles and frequency, execution order, change table and various counters in order to effect implementations of varying sequences of square waveforms. During operation, a microprocessor imports these operational parameters and produces a corresponding sequence of digital values. The digital values, together constituting a square waveform, are then converted into electrical current by a waveform generator and applied to an inductor in order to produce the resultant magnetic fields. The Edwards et al. device requires its microprocessor to execute several instructions in order to generate each digital value in real-time. In doing so, the microprocessor is occupied for several cycles per digital value produced and is accordingly restricted in terms of the frequency at which it can produce those values. As a result, Edward's device is inherently limited by its design to producing waveforms with frequencies far below the clock speed of its microprocessor, and a much faster and accordingly expensive microprocessor is required in order to overcome the limitation. Furthermore, Edward's device recalculates a change in waveform characteristics only after a session counter has reached a certain parameter value as reflected in a change table. Thus, the device is restricted to producing square waveforms in the interim, and uses up cycles when constantly comparing the counter to the change table, further restricting the frequency of the resultant waveforms.

It is therefore an object of the present invention to provide a novel portable electrotherapy device for generating specific low frequency pulsed magnetic fields that are used to modify a variety of physiological, neurological and behavioural conditions in vertebrates and invertebrates.

SUMMARY OF THE INVENTION

According to one aspect of the present invention there is provided an electrotherapy device for generating specifically designed low frequency pulsed magnetic fields (Cnp waveforms) comprising:

memory storing at least one digital Cnp waveform;

a digital to analog converter converting said at least one digital waveform into an analog Cnp waveform for application to a subject; and a processor communicating with said memory, said processor being responsive to operator input and conditioning said memory to output said at least one digital Cnp waveform directly to said digital to analog converter thereby to bypass said processor.

According to another aspect of the present invention there is provided a portable electrotherapy device for generating specifically designed low frequency pulsed magnetic fields (Cnp waveforms) comprising:

a controller including a compact housing, said housing having operator controls and an interface thereon and accommodating processing circuitry therein, said processor circuitry including:

memory storing a plurality of digital Cnp waveforms;

a digital to analog converter converting a selected one of said digital Cnp waveforms into an analog Cnp waveform for application to a subject; and a processor communicating with said memory, said processor being responsive to commands input via said operator controls and conditioning said memory to output a selected one of said digital Cnp waveforms directly to said digital to analog converter thereby to bypass said processor; and at least one set of coils coupled to said controller, said coils being worn by a subject and being responsive to said analog Cnp waveform thereby to apply said Cnp waveform to said subject.

Preferably, the memory is remotely programmable by a computer coupled to the controller via the interface. It is also preferred that the processor stores operating parameters used to control the output of the selected digital Cnp waveform to the digital to analog converter with the processor also being remotely programmable.

Preferably, the processing circuitry further includes an amplifier connected to the digital to analog converter for boosting the analog Cnp waveform prior to output to the coils. In one form, the set of coils includes a set of head coils. In this case, the digital Cnp waveforms are configured so that resulting analog Cnp waveforms provide shallow to deep brain stimulation when the head coils are worn by the subject. In another form, the set of coils includes a set of wrap coils. In this case, the digital Cnp waveforms are configured so that resulting analog Cnp waveforms provide localized deep tissue exposure when the wrap coils are worn by the subject.

According to a further aspect of the present invention, there is provided a portable electrotherapy device for generating specifically designed low frequency pulsed magnetic fields (Cnp waveforms) comprising:

a controller including a compact housing, said housing having user controls and an interface thereon and accommodating processing circuitry therein, said processor circuitry including:

memory storing a plurality of digital Cnp waveforms;

a digital to analog converter converting a selected one of said digital Cnp waveforms into an analog Cnp waveform for application to a subject; and a processor communicating with said memory, said processor being responsive to commands input via said operator controls and conditioning said memory to output a selected one of said digital Cnp waveforms directly to said digital to analog converter thereby to bypass said processor, and a coil coupled to said controller, said coil being worn by a subject and being responsive to said analog Cnp waveform thereby to apply said Cnp waveform to said subject. As will be appreciated, the present invention provides a portable electrotherapy device to deliver low frequency pulsed magnetic fields (Cnp waveforms) to a subject. Previously, the generation of low frequency pulsed magnetic fields required the use of expensive, bulky and heavy equipment connected to a computer, and operated by skilled technicians. The present device offers portable operation without connection to a separate computer and ease of operation, making the device usable by non-technical people.

The present invention also provides advantages in that since the digital Cnp waveforms stored in the memory are conveyed directly to the digital to analog converter under the control of the processor but not through the processor, analog Cnp waveforms can be generated at a higher speed and with better resolution.

BRIEF DESCRIPTION OF THE DRAWINGS

Embodiments of the present invention will now be described more fully with reference to the accompanying drawings in which.

DETAILED DESCRIPTION OF THE PREFERRED EMBODIMENTS

Figure 1:
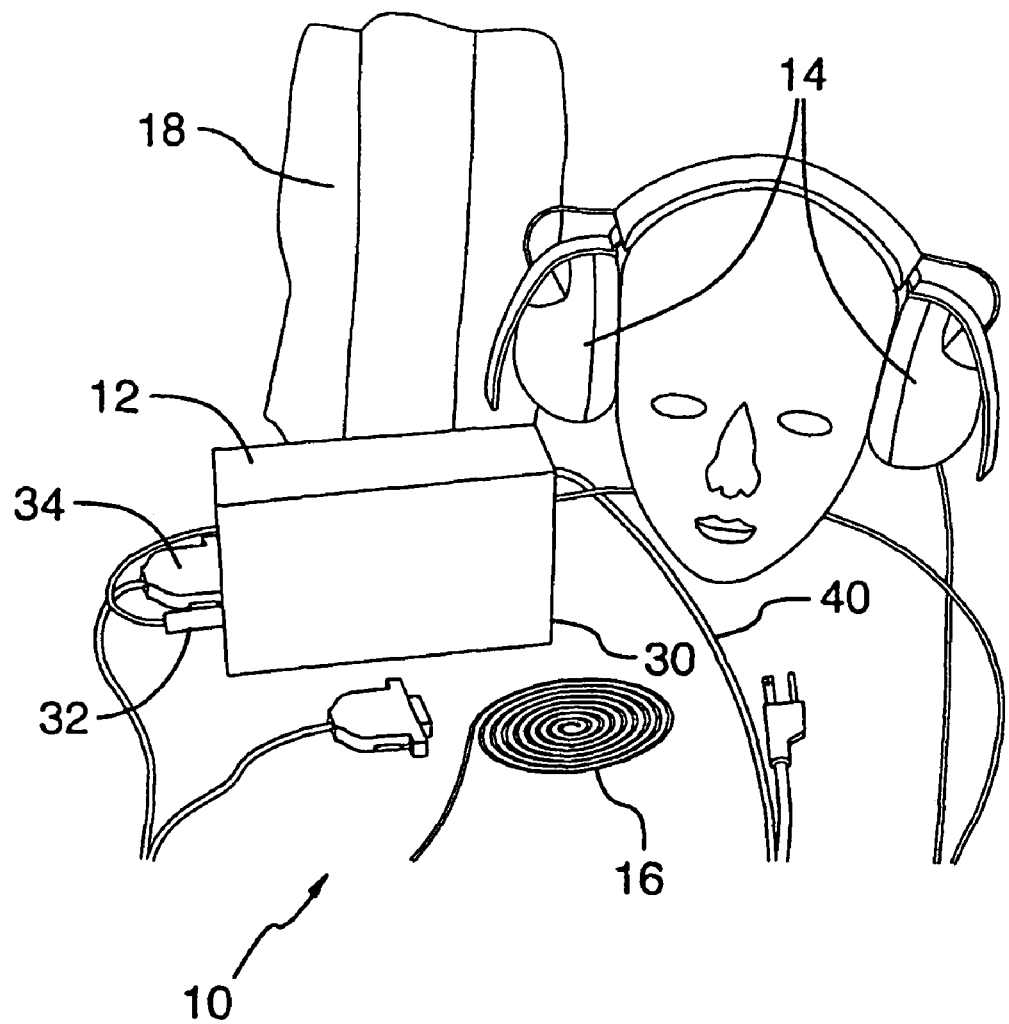
FIG. 1 is an illustration of a portable electrotherapy device in accordance with the present invention.

Turning now to FIG. 1, an illustration of a portable electrotherapy device for generating specifically designed low frequency pulsed magnetic fields (Cnp waveforms) in accordance with the present invention is shown and is generally identified by reference numeral 10. As can be seen, portable electrotherapy device 10 includes a microprocessor-based controller 12 and a plurality of coils connectable to the controller. In the present embodiment, the coils include a pair of head coils 14 and a pair of wrap coils 16, only one of which is shown for ease of illustration. As will be appreciated, the head coils 14 allow Cnp waveforms generated by the portable electrotherapy device to be applied to the brain tissue of a subject. The wrap coils 16 allow Cnp waveforms generated by the portable electrotherapy device to be applied to other area of a subject thereby to stimulate tissue. To facilitate application of Cnp waveforms to a subject's tissue, the wrap coils 16 are accommodated by holders that are worn by the subject to position properly the wrap coils on the subject's body. A knee wrap coil holder 18 to position the wrap coils 16 adjacent a subject's knee is shown for illustrative purposes. It is understood by one of skill in the art that while a pair of coils are shown as head coils or discussed with respect to the wrap coils, one coil may alternatively be used in either aspect.

Controller 12 includes a compact portable housing 30 having output jacks 32 into which either the head or wrap coils 14 or 16 are plugged to enable the controller 12 to drive the coils. The housing 30 also includes an RS-232 serial interface 34 to allow the controller 12 to be coupled to a remote computer (not shown). Controls and indicators, as will be described, are provided on the housing 30 enabling an operator to operate the electrotherapy device 10 in the desired manner. An electrical cord 40 extends from the housing 30 allowing the controller 12 to be powered by a conventional 110 VAC power supply.

Figure 2:
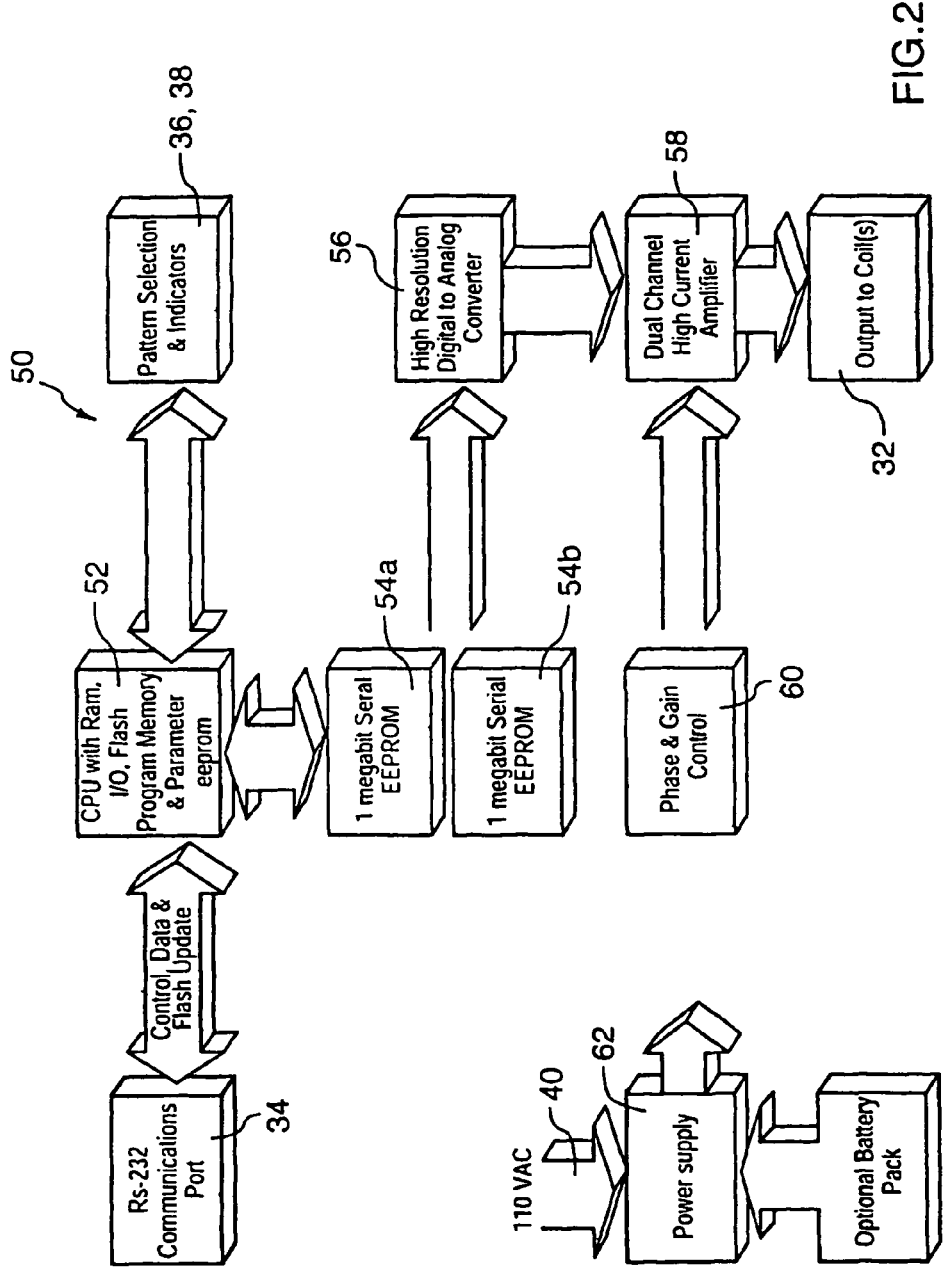
FIG. 2 is a block diagram of the portable electrotherapy device of FIG. 1.
Figure 3A:
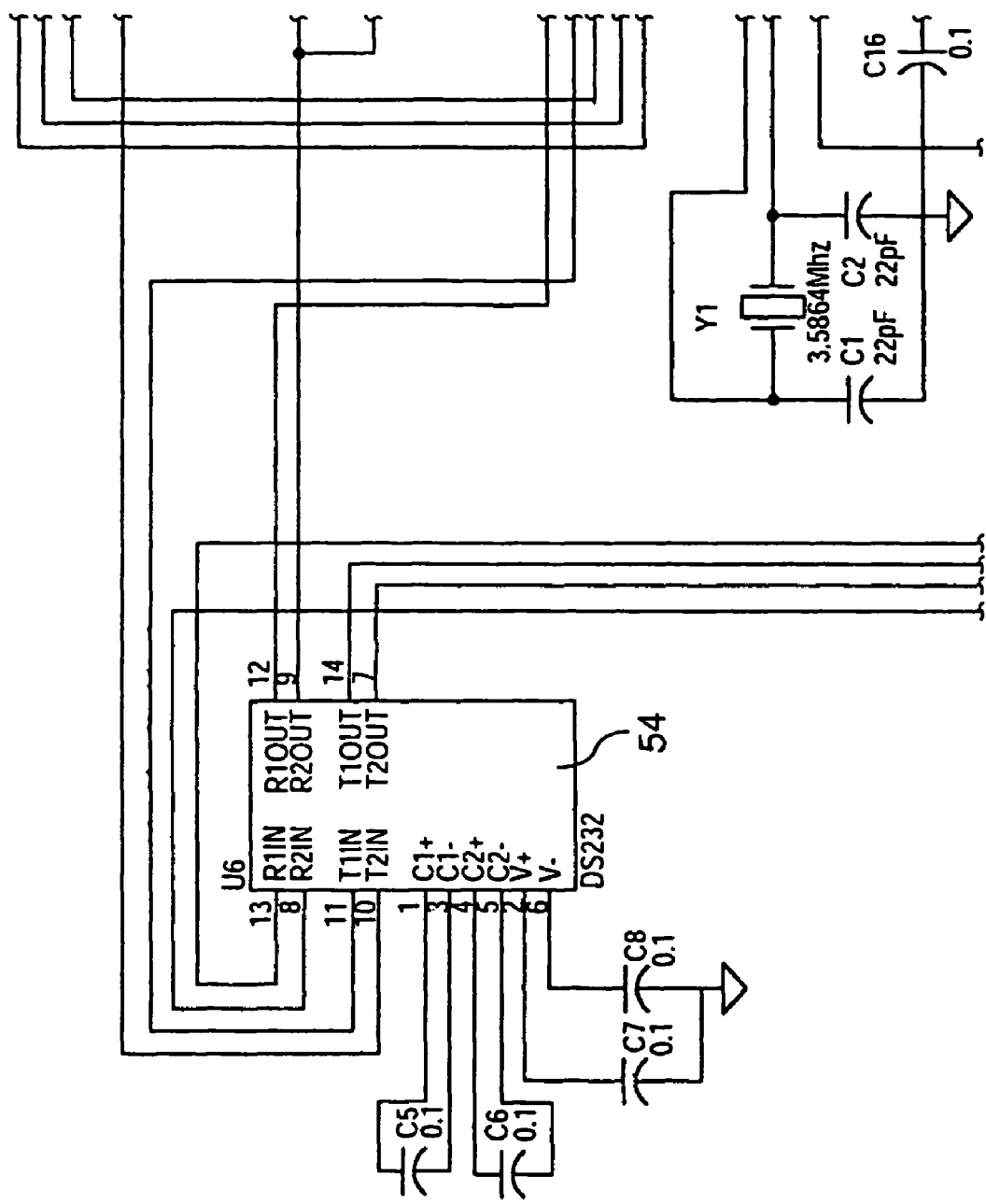
FIGS. 3A-3F are schematic diagrams
Figure 3B:
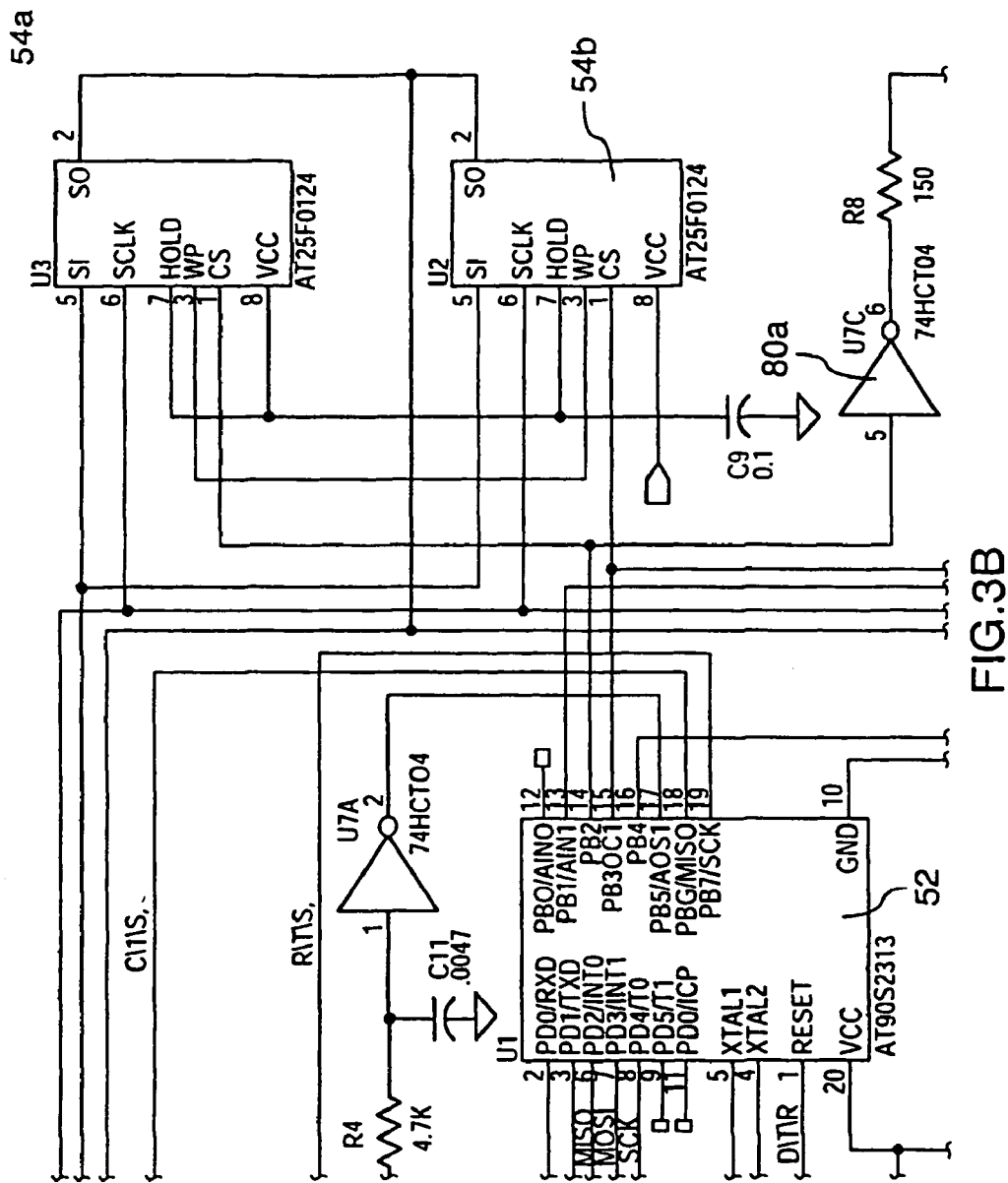
Figure 3C:
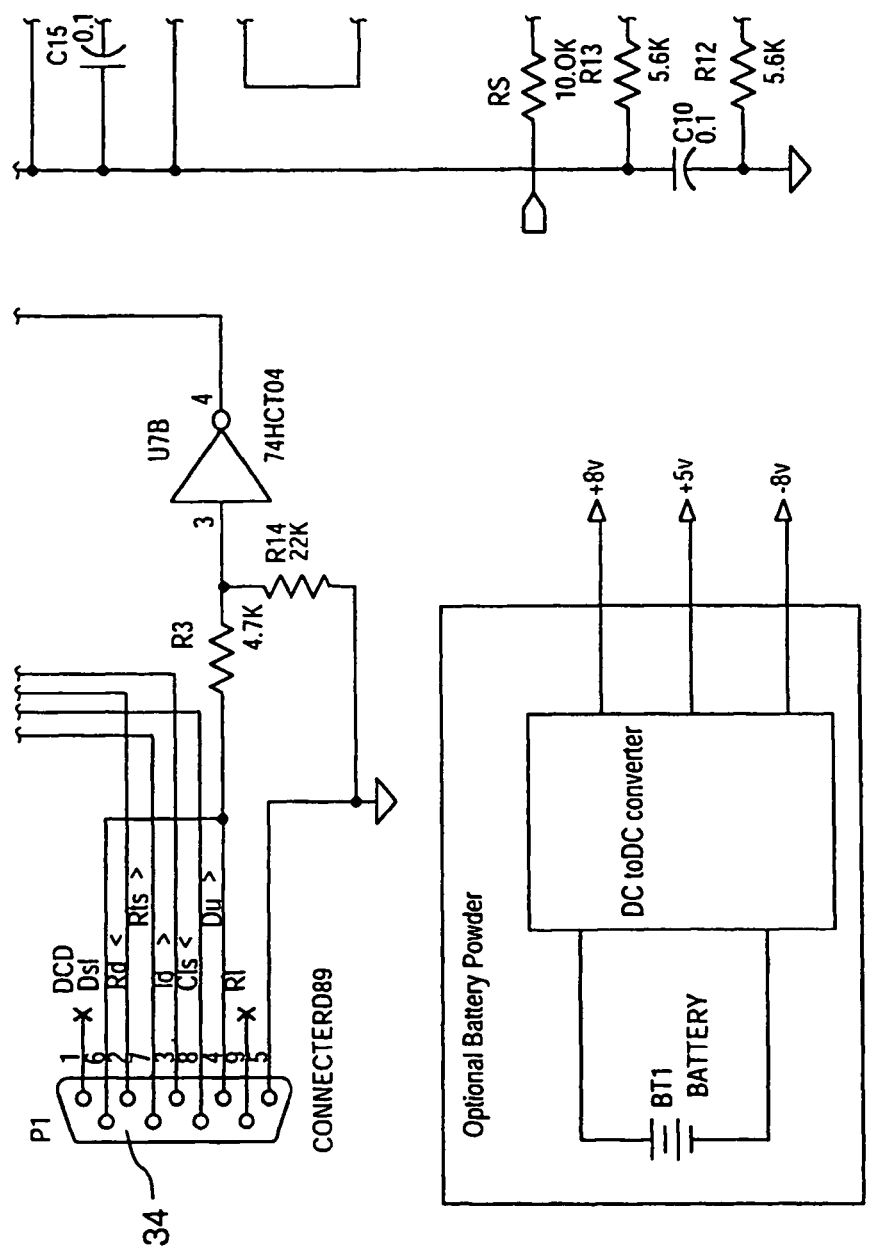
Figure 3D:
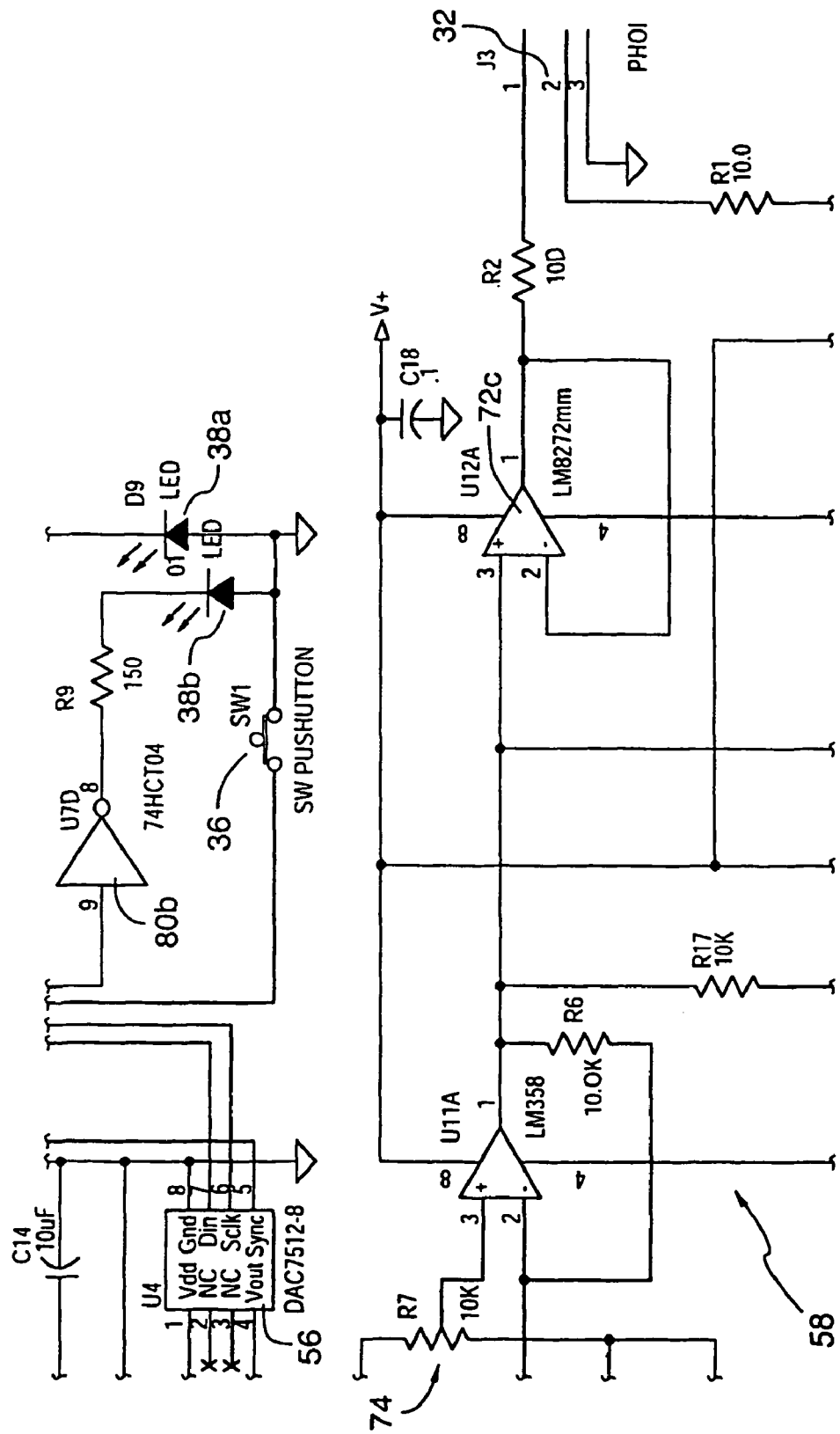
Figure 3E:
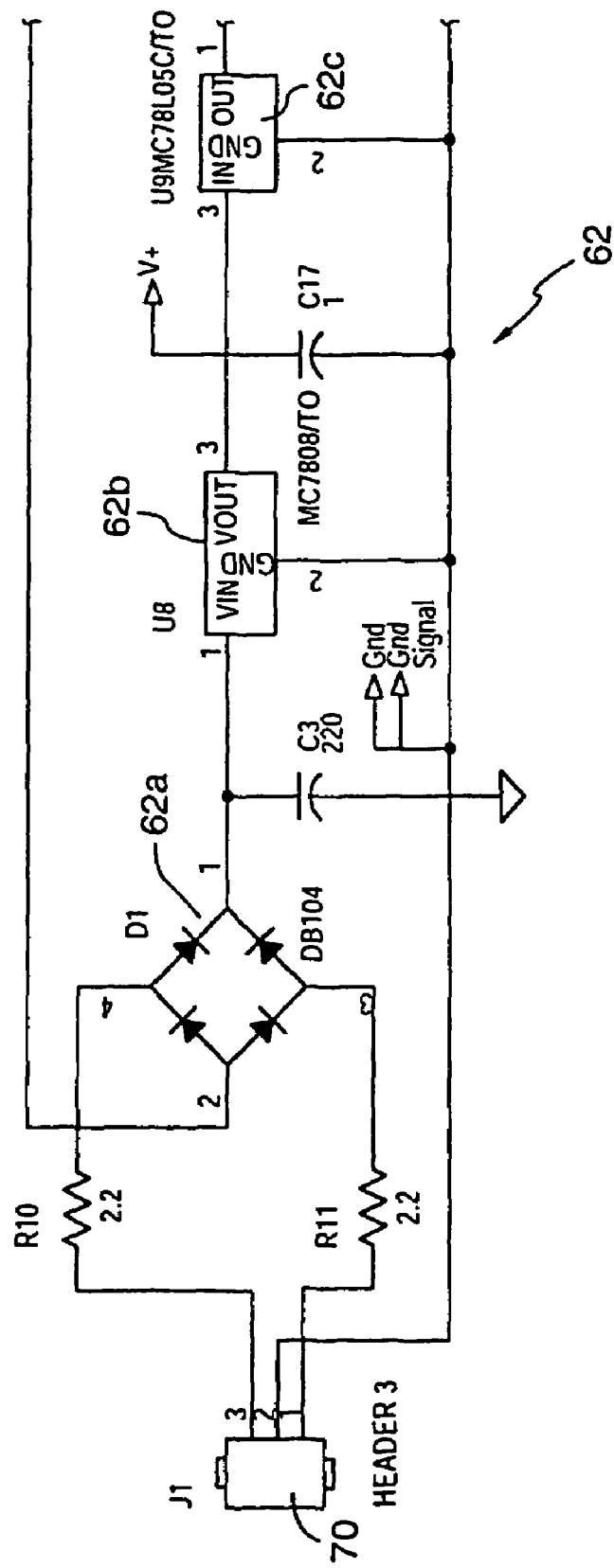
Figure 3F:
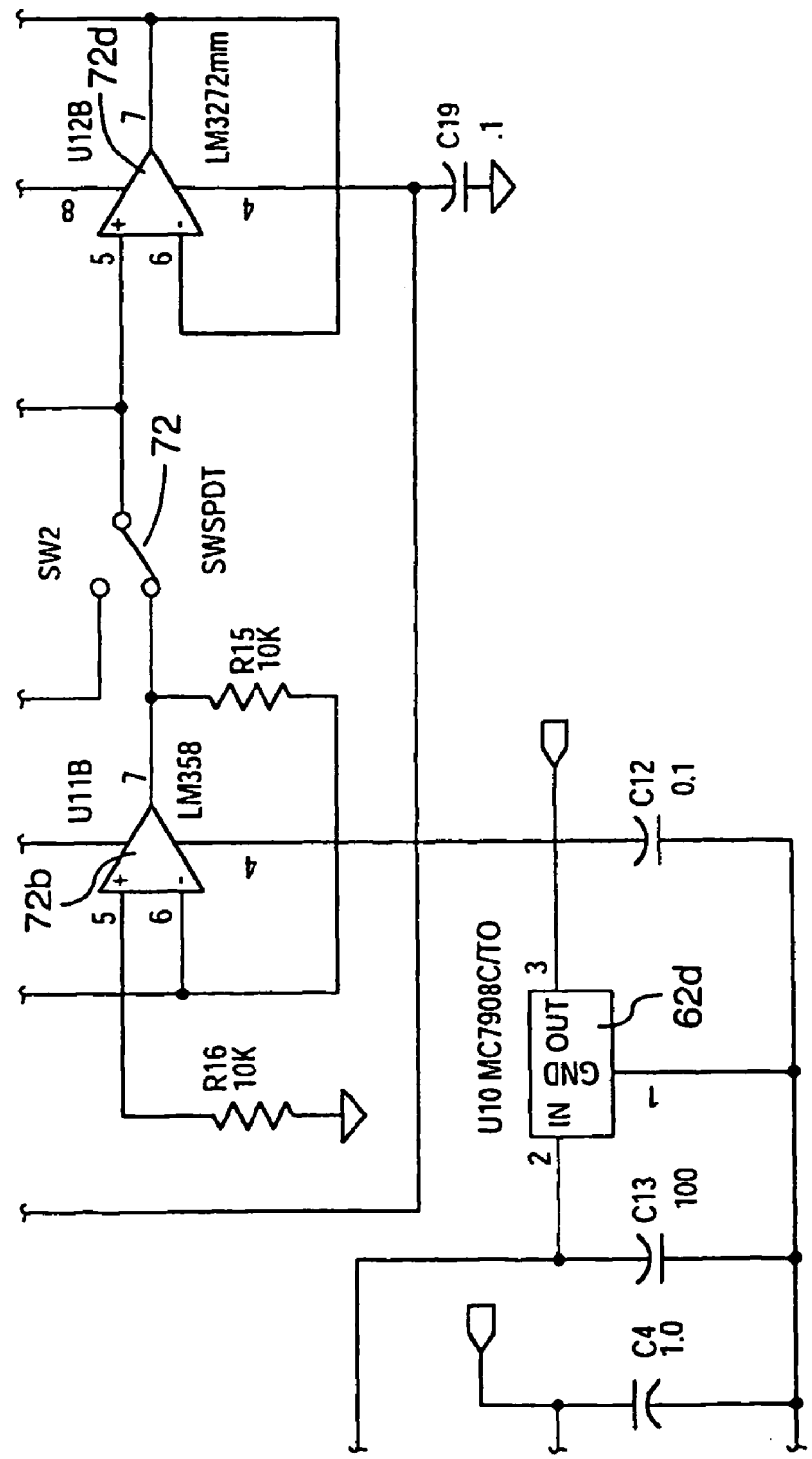
Figure 4:
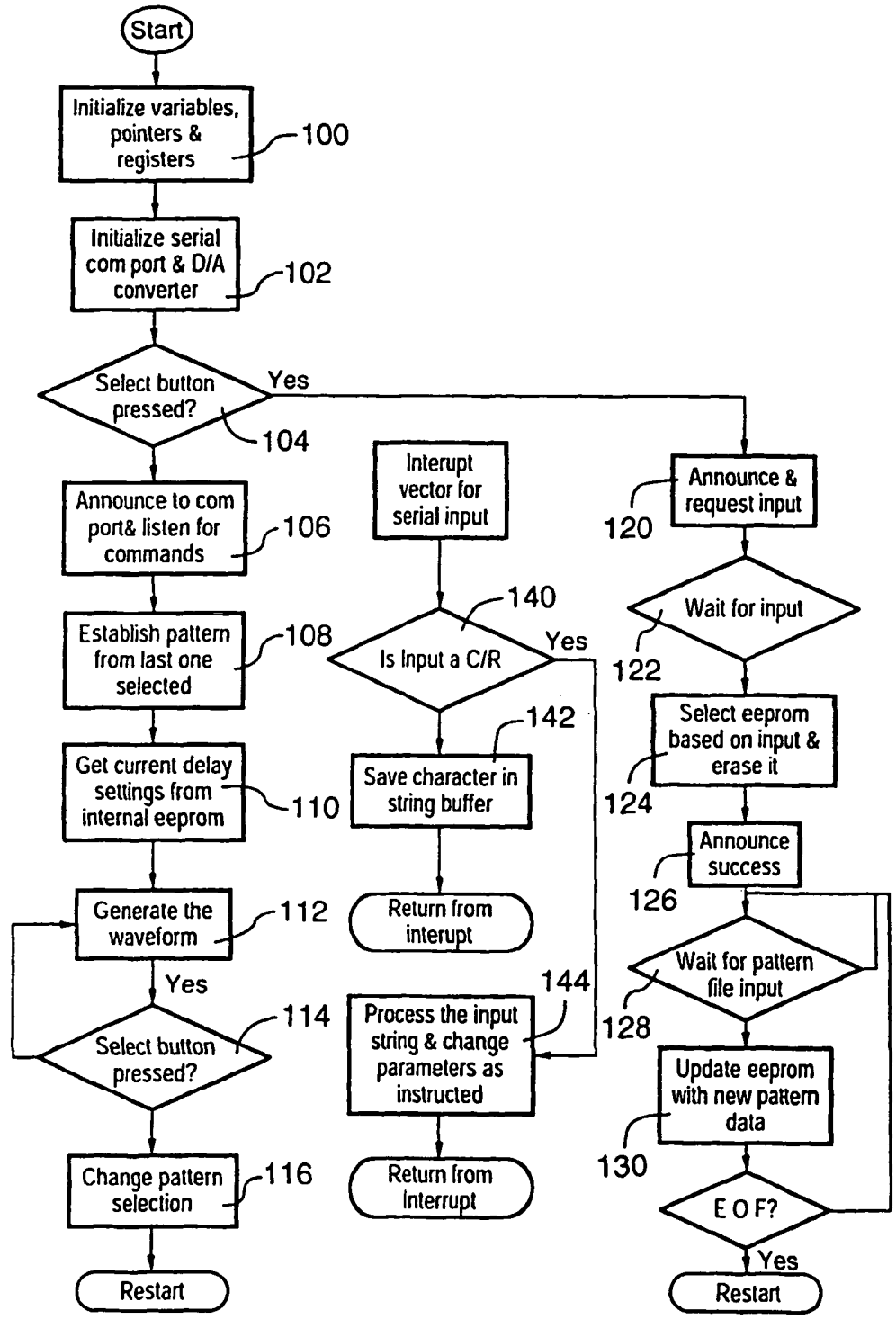
FIG. 4 is a flow chart showing the steps performed by the portable electrotherapy device of FIG. 1.

FIGS. 2 and 3 illustrate the circuitry 50 within the housing 30. As can be seen in FIG. 2, the circuitry includes a central processing unit (CPU) 52 with random access memory (RAM), input/output (I/O) memory, flash program memory and electrically erasable programmable read only memory (EEPROM). CPU 52 communicates with the serial interface 34, the controls and the indicators as well as with a pair of serial EEPROMs 54a and 54b. A high resolution digital to analog convertor (DAC) 56 communicates with the EEPROMs 54a and 54b and with a dual channel high current amplifier 58 that is responsive to phase and gain controls. The amplifier 58 provides analog output to the jacks 32 and hence to the coils. A fused power supply 62 receives input power from the AC power source and provides appropriate DC power to the circuitry 50.

Turning now to FIG. 3, the circuitry 50 is further illustrated. Power supply 62 is conventional includes a full wave rectifier 62a and a series of voltage regulators 62b, 62c and 62d respectively. The voltage regulators provide the DC voltages necessary to power the circuitry 50.

The EEPROMs 54a and 54b are coupled to the serial interface 34 via an RS232 converter 54. Each EEPROM 54a, 54b stores a different digital Cnp waveform table. The digital Cnp waveform tables are preloaded into the EEPROMs 54a and 54b by the remote computer via the serial interface 34. The digital Cnp waveform tables are characterized by bipolar decimal values that are assembled into analog Cnp waveforms using high resolution digital to analog conversion. The digital Cnp waveform table data is selected so that the portable electrotherapy device 10 generates Cnp waveforms similar to those described in U.S. Pat. No. 6,234,953 to Thomas et al., the contents of which are incorporated herein by reference. Specifically, the digital Cnp waveform table data is selected so that the resulting analog Cnp waveforms provide shallow to deep brain stimulation when the head coils 14 are used and localized deep tissue exposure when the wrap coils 16 are used.

The amplifier 58 includes a pair of channels, each channel having two amplifying stages. Each amplifying stage includes an input amplifier 72a, 72b and an output amplifier 72c, 72d. The amplifier 58 supplies enough current to drive the coils to provide a magnetic field density sufficient to deliver a Cnp waveforms having a 100 microTesla peak magnitude field flux density at 8 cm (16 cm between coils). The dual channels of the amplifier 58 permit in-phase or out-of-phase operation of multiple coil configurations.

The controls on the housing 30 include a power on/off switch 70 on one end panel of the housing 30 adjacent the electrical card 40. A push button switch 36 is located on the opposite end panel of the housing 30 adjacent the indicators 38a and 38b. The push button switch 36 allows an operator to select the desired Cnp waveform to be output by the electrotherapy device 10 or initiate a digital Cnp waveform table download as will be described. A phase switch 72 and a gain control switch 74 are also provided on the end panel adjacent the push button switch 36. The phase switch 72 allows the polarity of one of the output channels of the amplifier 58 to be inverted. The gain control switch 74 controls the gain of the amplifier 58 with a 5 to 1 range.

The EEPROM in the CPU 52 stores a number of digital Cnp waveform operating parameters such as point number, latency period and refractory period. The point number determines the size of the Cnp waveform to be generated by the portable electrotherapy device 10 by specifying the number of points in the digital Cnp waveform table that are used to create the output analog Cnp waveform. The latency period specifies the duration between successive points and the refractory period specifies the time between repeating Cnp waveforms. The digital Cnp waveform operating parameters are downloaded into the EEPROM of the CPU 52 by the remote computer via the serial interface 34 and RS232 converter 54.

The operation of the portable electrotherapy device 10 will now be described with reference to FIGS. 1 to 4. It will be assumed that the digital Cnp waveform tables and operating parameters have been loaded into the EEPROMs and that the coils to be used to simulate the subject are worn by the subject at the appropriate locations. When the controller 12 is powered, the CPU 52 initializes its variables, pointers and registers (step 100) and then initializes the serial interface 34 and the DAC 56 (step 102). If the operator conditions the controller 12 to generate a Cnp waveform by pressing switch 36 (step 104), the CPU 52 selects the EEPROM 54a, 54b that is to be used to generate the Cnp waveform (steps 106 and 108). The CPU 52 also illuminates the indicator 38a, 38b associated with the selected EEPROM via an amplifier 80a, 80b to provide the operator with visual feedback concerning the selected digital Cnp waveform table. The CPU 52 then loads the digital Cnp waveform operating parameters stored in its EEPROM (step 110). Following this, the CPU 52 conditions the EEPROM 54a, 54b to transfer the digital Cnp waveform table to the DAC 56 without the digital Cnp waveform table data passing through the CPU 52. The DAC 56 in turn converts the digital Cnp waveform table into an analog signal (i.e. the Cnp waveform) that is applied to the amplifier 58. The amplifier 58 in turn boosts the DAC output and supplies the output analog Cnp waveform to the coils via the output jacks 34 (step 112). The Cnp waveform generation process continues as specified by the refractory period parameter. If during this process the operator presses the switch 36 again, the CPU 52 conditions the other EEPROM to output its digital Cnp waveform table stored therein and the above steps are re-performed (steps 114 and 116). Beneficially, switch 36 is connected via an interrupt line to CPU 52 so that it can immediately respond when switch 36 is pressed, rather than wait until the end of a wave.

As will be appreciated, during Cnp waveform generation, since the digital Cnp waveform table is transferred directly from the EEPROM 54a, 54b to the DAC 56 under the timing control of the CPU 52, but does not pass through the CPU, many CPU instruction cycles are eliminated. This is due to the fact that the need to read serial digital Cnp waveform table data into the CPU and then write the serial digital Cnp waveform table data to the DAC 56 is avoided. The CPU 52 of course has the ability to read and write to the EEPROMs 54a, 54b and the DAC 56 during periods where no Cnp waveform is being generated. This data transfer method provides for a higher speed, which produces finer time resolution for the output Cnp waveforms.

At step 104, if the operator conditions the controller 12 to receive digital Cnp waveform table data from the remote computer by processing the switch 36, the CPU 52 initializes the EEPROMs 54a and 54b and the serial interface and awaits input digital Cnp waveform tables from the remote computer (steps 120 and 122). When the CPU 52 receives an overwrite command from the remote computer, the CPU 52 erases the appropriate digital Cnp waveform table from the selected EEPROM 54a, 4b and notifies the remote computer (steps 124 and 126). The CPU then awaits receipt of the replacement digital Cnp waveform table (step 128). When the digital Cnp waveform table is received from the remote computer, the CPU writes the digital Cnp waveform table to the selected EEPROM (step 130).

If the operator conditions the controller 12 to receive updated digital Cnp waveform operating parameters, the CPU 52 monitors the remote computer for digital Cnp waveform operating parameter input. The digital Cnp waveform operating parameter input is in the form of character strings that are serially loaded into the CPU 52 and stored in a string buffer. Once the digital Cnp waveform operating parameter data is completely received, the CPU 52 stores the new digital Cnp waveform operating parameters into its EEPROM.

Although the controller 12 is shown as being supplied with power from an AC power source, those of skill in the art will appreciate that the controller may also be fitted with a rechargeable power supply as shown in FIGS. 2 and 3, an AC adapter or alternative power supply. For a controller 12 that employs, for instance, batteries, it may be useful to incorporate a battery-power detection circuit, software and an indicator to show a user the power status with the ultimate goal of preventing corruption of the EEPROM parameters due to a low or unusable battery. In addition, the controller 12 need not be remotely programmable. In this case the EEPROMs 54a and 54b are pre-programmed with the digital Cnp waveform tables of interest and the serial interface 34 is unnecessary.

It may be envisaged by one of skill in the art to couple an alphanumeric display such as an LCD module to controller 12 in order to display device operational information. To this end, such a display may be used to show to a user any of the active pattern parameters, the name of the pattern and its refractory status (using, for example, a blinking "*"). The display may further be used to replace the pattern indicator LEDs 38a and 38b, reducing unnecessary power consumption, or indicate battery-power status.

If desired the circuitry 50 may be provided with a balance control to balance the output of the amplifier 58. Such a balance control could be in the form of a variable potentiometer inserted at the input of the two output amplifiers 72c, 72d with the center lead grounded so that adjustment of the potentiometer reduces the gain of one output amplifier and increases the gain of the other output amplifier.

Although preferred embodiments of the present invention have been described, those of skill in the art will appreciate that variations and modifications may be made without departing from the spirit and scope thereof as defined by the appended claims.

What is claimed is:

1. An electrotherapy device for generating specifically designed low frequency pulsed magnetic fields (Cnp waveforms) comprising:
    a memory storing at least one digital Cnp waveform;
    a digital to analog converter converting said at least one digital Cnp waveform into an analog Cnp waveform for application to a subject; and
    a processor communicating with said memory, said processor being responsive to operator input and adapted to coordinate said digital to anlog converter and said memory for transmission of said at least one digital Cnp waveform directly from said memory to said digital to analog converter thereby to bypass said processor.

2. An electrotherapy device according to claim 1 wherein said memory stores a plurality of digital Cnp waveforms, and a selected one of said digital Cnp waveforms is transmitted.

3. An electrotherapy device according to claim 2 further comprising an amplifier connected to said digital to analog converter for boosting said analog Cnp waveform and a pair of coils connected to said amplifier for applying said analog Cnp waveform to said subject.

4. An electrotherapy device according to claim 3 wherein said pair of coils includes a set of head coils, said digital Cnp waveforms being configured so that said analog Cnp waveforms provide shallow to deep brain stimulation when said head coils are worn by a subject.

5. An electrotherapy device according to claim 3 wherein said pair of coils includes a set of wrap coils, said digital Cnp waveforms being configured so that said analog Cnp waveforms provide localized deep tissue exposure when said wrap coils are worn by a subject.

6. An electrotherapy device according to claim 3 wherein said processor stores operating parameters used to control the transmission of said selected digital Cnp waveform to said digital to analog converter.

7. An electrotherapy device according to claim 6 wherein said operating parameters include at least one of latency and refractory periods.

8. An electrotherapy device according to claim 6 wherein said memory is remotely programmable.

9. An electrotherapy device according to claim 8 wherein said operating parameters are remotely programmable.

10. A portable electrotherapy device for generating specifically designed low frequency pulsed magnetic fields (Cnp waveforms) comprising:
    a controller including a compact housing, said housing having user controls and an interface thereon and accommodating processing circuitry therein, said processor circuitry including:
    a memory storing a plurality of digital Cnp waveforms;
    a digital to analog converter converting a selected one of said digital Cnp waveforms into an analog Cnp waveform for application to a subject; and
    a processor communicating with said memory, said processor being responsive to commands input via said operator controls and adapted to coordinate said digital to analog converter and said memory for transmission of a selected one of said digital Cnp waveforms directly to said digital to analog converter from said memory thereby to bypass said processor; and
    at least one set of coils coupled to said controller, said coils being worn by a subject and being responsive to said analog Cnp waveform thereby to apply said Cnp waveform to said subject.

11. A portable electrotherapy device according to claim 10 wherein said memory is remotely programmable by a computer coupled to said controller via said interface.

12. A portable electrotherapy device according to claim 11 wherein said processor stores operating parameters used to control the transmission of said selected digital Cnp waveform to said digital to analog converter.

13. A portable electrotherapy device according to claim 12 wherein said processor is remotely programmable by a computer coupled to said controller via said interface.

14. A portable electrotherapy device according to claim 13 further comprising an amplifier connected to said digital to analog converter for boosting said analog Cnp waveform prior to output to said coils.

15. A portable electrotherapy device according to claim 14 wherein said set of coils includes a set of head coils, said digital Cnp waveforms being configured so that resulting analog Cnp waveforms provide shallow to deep brain stimulation when said head coils are worn by a subject.

16. A portable electrotherapy device according to claim 14 wherein said set of coils includes a set of wrap coils, said digital Cnp waveforms being configured so that resulting analog Cnp waveforms provide localized deep tissue exposure when said wrap coils are worn by a subject.

17. A portable electrotherapy device according to claim 13 wherein said operating parameters include at least one of latency and refractory periods.

18. A portable electrotherapy device for generating specifically designed low frequency pulsed magnetic fields (Cnp waveforms) comprising:
    a controller including a compact housing, said housing having user controls and an interface thereon and accommodating processing circuitry therein, said processor circuitry including:
    a memory storing a plurality of digital Cnp waveforms;
    a digital to analog converter converting a selected one of said digital Cnp waveforms into an analog Cnp waveform for application to a subject; and
    a processor communicating with said memory, said processor being responsive to commands input via said operator controls and adapted to coordinate said digital to analog converter and said memory for transmission of a selected one of said digital Cnp waveforms directly to said digital to analog converter from said memory thereby to bypass said processor; and a coil coupled to said controller, said coil being worn by a subject and being responsive to said analog Cnp waveform thereby to apply said Cnp waveform to said subject.

19. A portable electrotherapy device according to claim 18 wherein said memory is remotely programmable by a computer coupled to said controller via said interface.

20. A portable electrotherapy device according to claim 19 wherein said processor stores operating parameters used to control the transmission of said selected digital Cnp waveform to said digital to analog converter.

21. A portable electrotherapy device according to claim 20 wherein said processor is remotely programmable by a computer coupled to said controller via said interface.

22. A portable electrotherapy device according to claim 21 further comprising an amplifier connected to said digital to analog converter for boosting said analog Cnp waveform prior to output to said coil.

23. A portable electrotherapy device according to claim 22 further comprising a second coil wherein said coils are head coils, said digital Cnp waveforms being configured so that resulting analog Cnp waveforms provide shallow to deep brain stimulation when said head coils are worn by a subject.

24. A portable electrotherapy device according to claim 22 further comprising a second coil wherein said coils are wrap coils, said digital Cnp waveforms being configured so that resulting analog Cnp waveforms provide localized deep tissue exposure when said wrap coils are worn by a subject.

25. A portable electrotherapy device according to claim 21 wherein said operating parameters include at least one of latency and refractory periods.

* * * * *